US006730715B2

(12) United States Patent
Jia

(10) Patent No.: US 6,730,715 B2
(45) Date of Patent: May 4, 2004

(54) DENTAL RESTORATIVE COMPOSITION, DENTAL RESTORATION, AND A METHOD OF USE THEREOF

(75) Inventor: Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 0 days.

(21) Appl. No.: 10/190,868

(22) Filed: Jul. 8, 2002

(65) Prior Publication Data

US 2003/0083400 A1 May 1, 2003

Related U.S. Application Data

(60) Provisional application No. 60/303,677, filed on Jul. 6, 2001.

(51) Int. Cl.[7] .............................. C08K 3/26; C08K 3/18; A61F 2/00
(52) U.S. Cl. ........................ 523/115; 523/116; 523/118; 524/430; 524/433; 524/442; 524/443; 524/495; 524/701; 524/706; 524/710; 524/712; 524/800; 524/804; 526/323.1
(58) Field of Search ................................. 523/115, 116, 523/118; 524/430, 433, 442, 443, 495, 701, 706, 710, 712, 800, 804; 526/323.1

(56) References Cited

U.S. PATENT DOCUMENTS

| | | | |
|---|---|---|---|
| 3,066,112 A | 11/1962 | Bowen ........................ 260/41 |
| 3,179,623 A | 4/1965 | Bowen ........................ 260/47 |
| 3,194,784 A | 7/1965 | Bowen ........................ 260/41 |
| 3,751,399 A | 8/1973 | Lee, Jr. et al. ................. 260/47 |
| 3,926,906 A | 12/1975 | Lee, II et al. ............. 260/42.53 |
| 4,544,359 A | 10/1985 | Waknine ..................... 523/115 |
| 4,547,531 A | 10/1985 | Waknine ..................... 523/116 |
| 5,276,068 A | 1/1994 | Waknine ...................... 522/28 |
| 5,859,089 A | 1/1999 | Qian .......................... 523/116 |
| 5,962,550 A | 10/1999 | Akahane et al. ............. 523/116 |
| 6,004,390 A | 12/1999 | Pflug et al. .................. 106/35 |
| 6,013,694 A | 1/2000 | Jia et al. ..................... 523/116 |
| 6,127,451 A | 10/2000 | Qian .......................... 523/116 |
| 6,136,885 A | 10/2000 | Rusin et al. ................. 523/116 |
| 6,214,101 B1 | 4/2001 | Nakaseko .................... 106/35 |
| 6,506,816 B1 * | 1/2003 | Ario et al. ................... 523/116 |

* cited by examiner

Primary Examiner—Kriellion A. Sanders
(74) Attorney, Agent, or Firm—Cantor Colburn LLP

(57) ABSTRACT

A curable dental restorative composition comprising about 1 to about 90 wt %, based on the total weight of the composition, of a filler component, the filler component comprising about 10 to 100 wt %, based on the total weight of the filler component, of a surface reactive glass component; about 1 to about 50 wt %, based on the total weight of the composition, of water; and about 10 to about 97 wt %, based on the total weight of the composition, of a curable organic component, comprising about 50 to about 99 wt %, based on the total weight of the curable organic component, of an ethylenically unsaturated resin component, about 1 to about 50 wt %, based on the total weight of the curable organic component, of an ethylenically unsaturated phosphoric acid ester; and about 0.01 to about 5 wt % of a curing system.

20 Claims, No Drawings

DENTAL RESTORATIVE COMPOSITION, DENTAL RESTORATION, AND A METHOD OF USE THEREOF

CROSS REFERENCE TO RELATED APPLICATIONS

This application claims the benefits of U.S. Provisional Patent Application Ser. No. 60/303,677 filed Jul. 6, 2001, which is fully incorporated herein by reference.

BACKGROUND

This invention relates to composite materials for restorative dentistry, and more particularly to composites useful as reconstructive materials and restorative materials for tooth cavity filling, lining or basing, cementation, orthodontic bracket bonding, laminate veneers, dental adhesives, cements, sealants, and the like.

In recent years, materials used for dental restorations have comprised principally acrylic resin systems, that is, acrylate or methacrylate polymers. Typical acrylic resin systems are disclosed in U.S. Pat. No. 3,066,112 to Bowen, U.S. Pat. No. 3,179,623 to Bowen, U.S. Pat. No. 3,194,784 to Bowen, U.S. Pat. No. 3,751,399 to Lee et al. and U.S. Pat. No. 3,926,906 to Lee et al. An especially important methacrylate monomer is the condensation product of bisphenol A and glycidyl methacrylate, 2,2'-bis [4-(3-methacryloxy-2-hydroxy propoxy)-phenyl]-propane ("Bis-GMA"). Urethane dimethacrylate ("UDMA"), polyurethane dimethacrylate ("PUDMA") are also commonly used as a principal polymer in dental restoratives of this type.

Since Bis-GMA, PUDMA, and other resins are highly viscous at room temperature, they are generally diluted with an acrylate or methacrylate monomer having a lower viscosity, such as trimethylol propyl trimethacrylate, 1,6-hexanediol dimethacrylate, 1,3-butanediol dimethacrylate, and the like. Other dimethacrylate monomers, such as ethylene glycol dimethacrylate, diethylene glycol dimethacrylate, triethylene glycol dimethacrylate, polyethylene glycol dimethacrylate (PEGDMA) and tetraethylene glycol dimethacrylate, are also in general use as diluents.

Because acrylic resin systems exhibit high coefficients of thermal expansion relative to the coefficient of thermal expansion of the tooth structure, these substances by themselves are less than satisfactory. The disparity in thermal expansion coupled with high shrinkage upon polymerization, results in poor marginal adaptability, and ultimately leads to secondary decay. Furthermore, the wear and abrasion characteristics and the overall physical, mechanical, and optical properties of these unfilled acrylic resinous materials is poor. "Composite acrylic dental restorative materials" containing acrylate or methacrylate resins and fillers were thus developed, the fillers generally comprising inorganic materials based on silica, silicate based glasses, or quartz.

Another type of dental restorative is a "glass ionomer", wherein a poly(carboxylic acid) (such as a homo- or co-polymer of acrylic acid) is reacted with a fluoride ion leachable species (such as a fluoroaluminosilicate glass) in the presence of water to yield a crosslinked network structure. Because of the incorporation of the fluoride ion leachable species, glass ionomers are capable of providing long-term fluoride release.

Combinations of the various components of composite acrylic dental restoratives and glass ionomers have also been described. These hybrid materials generally fall into two classes, one referred to as "resin modified glass ionomers" (hereinafter "RMGIs") and the other as "compomers".

RMGIs retain most of the characteristics of conventional glass ionomers in that water is an essential ingredient. RMGI accordingly comprise a water-miscible acidic polymer, a curing system, and finely divided acid-reactive fillers. Three cure mechanisms are available: an acid-base setting reaction of the conventional glass ionomer type, photo curing using photo initiators, and chemical curing using redox initiators via free-radical polymerization of the polymerizable vinyl groups. The three-way curing mechanism facilitates thorough, uniform cure and retention of good clinical properties. RMGI materials can be clinically applied using conventional techniques and possess improved mechanical properties compared to conventional glass ionomers. However, their application is still limited to use in low stress bearing areas of the mouth due to their inadequate mechanical strength and wear resistance. Another drawback is that RMGI restoratives, once placed in a restoration, tend to absorb excessive and uncontrolled amounts of water, causing crowns cemented with RMGIs to fracture due to excessive hygroscopic expansion.

The second type of hybrid material, compomers, comprise an acrylate or methacrylate monomer containing acid functional groups, a reactive fluoroaluminosilicate glass, and a curing system. They may also contain other copolymerizable acrylate and methacrylate monomers that do not contain acid functional groups. Water is absent from the composition; it is in an anhydrous (non-aqueous) form. The primary setting reaction of a compomer is free radical photo polymerization involving the vinyl functional groups. This provides the immediate strength and resistance needed in the oral cavity. In addition to long-term fluoride release, another desirable characteristic of compomers is the ability to absorb a small amount of water and, as a result, expand slightly to alleviate the shrinkage stress caused by the polymerization of the acrylate or methacrylate resin, thus contributing to good marginal integrity. However, improvements in mechanical strength and wear resistance are still desirable in order to provide satisfactory use, particularly as anterior/posterior restoratives.

SUMMARY OF THE INVENTION

The above-described drawbacks and disadvantages are alleviated by a curable dental restorative composition comprising about 1 to about 90 wt %, based on the total weight of the dental restorative composition, of a filler component, the filler component comprising about 10 to 100 wt %, based on the total weight of the filler component, of a surface reactive glass component, and up to about 90 wt %, based on the total weight of the filler component, of other organic or inorganic filler; about 1 to about 50 wt %, based on the total weight of the composition, of water; and about 10 to about 97 wt %, based on the total weight of the composition, of a curable organic component, comprising about 50 to about 99 wt %, based on the total weight of the curable organic component, of an ethylenically unsaturated resin component, about 1 to about 50 wt %, based on the total weight of the curable organic component, of an ethylenically unsaturated phosphoric acid ester; and about 0.01 to about 5 wt %, based on the total weight of the curable organic component, of a curing system.

A method of using the dental restorative composition and a dental restoration are also disclosed. Such compositions are useful for a variety of dental treatments and restorative functions including cavity fillings, adhesives, sealants, luting agents or cements, orthodontic bonding materials and sealants, and other dental restoratives and dental restorations. The above described and other features are exemplified by the following detailed description.

DETAILED DESCRIPTION OF THE PREFERRED EMBODIMENTS

An improved dental restorative is formed from a composition that comprises a curable organic component, a catalyst system, a surface reactive glass, and water. The curable organic component comprises an ethylenically unsaturated monomer or oligomer, wherein the unsaturation is preferably derived from acrylate or methacrylate groups. The curable component also comprises a curable, ethylenically unsaturated phosphoric acid ester component, for example, an acrylate terminated phosphoric acid ester or methacrylate terminated phosphoric acid ester. The dental restorative composition may be provided as a single admixture of components to the practitioner, even more preferably in the form of uniform, mixed phase. Alternatively, the curing system and/or other components may be provided to the practitioner separately as part of a multi-component system.

Acrylate and methacrylate monomers and oligomers for use as the ethylenically unsaturated resin component are known in the art, and may include the viscous acrylate or methacrylate monomers such as those disclosed in U.S. Pat. No. 3,066,112 to Bowen, U.S. Pat. No. 3,179,623 to Bowen, U.S. Pat. No. 3,194,784 to Bowen, U.S. Pat. No. 3,751,399 to Lee et al., U.S. Pat. No. 3,926,906 to Lee et al., and commonly assigned U.S. Pat. No. 5,276,068 and U.S. Pat. No. 5,444,104 to Waknine, all of which are incorporated herein by reference. Other acrylate- or methacrylate-containing monomers or oligomers include, but are not limited to, polyurethane dimethacrylate (PUDMA), diurethane dimethacrylate (DUDMA), and other monomers and oligomers known in the art. A useful oligomer is disclosed in U.S. Pat. Nos. 5,276,068 and 5,444,104 to Waknine, being a polycarbonate dimethacrylate (PCDMA) which is the condensation product of two parts of a hydroxyalkyl-methacrylate and 1 part of a bis(chloroformate). Another advantageous resin for use in the curable resin component and having lower water sorption characteristics is an ethoxylated bisphenol A dimethacrylate (EBPDMA) as disclosed in U.S. Pat. No. 6,013,694.

These viscous polymerizable components, i.e., DUDMA, PUDMA, Bis-GMA, PCDMA, EBPDAM, and the like, may comprise up to about 98 weight percent (wt %) of the total weight of the curable organic component. Within this range, a concentration of less than or equal to about 80 wt %, based on the total weight of the curable organic component, may also be used. Also preferred within this range is a concentration of greater than or equal to about 2 wt %, greater than or equal to about 20 wt %, with greater than or equal to about 50 wt %, based on the total weight of the total curable organic component, also being useful.

Also included within the scope of the curable, ethylenically unsaturated resin component are polymers having at least one, preferably multipl, carboxylic acid group(s). Such polymers are preferably themselves co-curable, i.e., comprise ethylenic unsaturation, and include those suitable for use with glass ionomer cements, for example, polycarboxylic acids such as homopolymers of itaconic, acrylic or methacrylic acid, or copolymers comprising itaconic, acrylic or methacrylic acid, or mixtures thereof. When used, these polymers are present in amount of up to about 30 wt %, preferably about 1 to about 30 wt %, based on the weight of the total curable organic component.

In addition to the aforementioned monomers, oligomers, and polymers, the curable, ethylenically unsaturated resin component can further include a diluent component, usually an acrylate or methacrylate monomer, preferably to increase the surface wettability of the composition and/or to decrease the viscosity of the curable, ethylenically unsaturated resin component. Suitable diluent monomers include those known in the art such as hydroxy alkyl methacrylates, for example 2-hydroxyethyl methacrylate and 2-hydroxypropyl methacrylate; ethylene glycol methacrylates, for example, ethylene glycol methacrylate, diethylene glycol methacrylate, tri(ethylene glycol) dimethacrylate, and tetra(ethylene glycol) dimethacrylate; and diol dimethacrylates, such as butanedioldimethacrylate, dodecanedioldimethacrylate, 1,6-hexanedioldimethacrylate, and the like. Tri(ethylene glycol) dimethacrylate (TEGDMA) is particularly preferred.

Diluent monomers, when present, are incorporated into the curable, ethylenically unsaturated resin component in an amount of up to about 100 wt %, based on the total weight of the ethylenically unsaturated resin component. Within this range, a concentration of less than or equal to about 90 wt % can be used, with less than or equal to about 70 wt %, more preferred. Also preferred within this range is a concentration of greater than or equal to about 10 wt %, or greater than or equal to about 20 wt %, based on the total weight of the total curable resin component.

The relative amounts of viscous monomers or oligomers, carboxylated polymers, and/or diluent monomers depends on the intended use of the restorative compositions. For example, a filling material will comprise a higher amount of viscous monomer, whereas an adhesive composition will comprise a higher relative amount of diluent monomer. Such adjustments are readily made by those of ordinary skill in the art. However, it is to be understood that the total weight of the ethylenically unsaturate resin component comprises about 50 to about 99 wt % of the total curable organic component.

The curable organic component further comprises a phosphoric acid ester, preferably a phosphoric acid ester that contains at least one moiety co-curable with the ethylenically unsaturated resin component. Preferably, the phosphoric acid ester component includes an acrylate terminated phosphoric acid ester or methacrylate terminated phosphoric acid ester. One preferred methacrylate terminated phosphoric acid ester is of the formula:

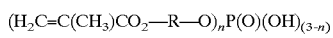

$(H_2C=C(CH_3)CO_2-R-O)_nP(O)(OH)_{(3-n)}$ wherein n=1 or 2 and R is an alkyl or aryl group having 1 to about 36 carbon atoms, preferably 1 to about 12, and more preferably 2 to about 4 carbon atoms. R may be subsituted or unsubstituted with, for example ether groups, hydroxyl, groups, and the like. A preferred ester is 2-(methacryloyloxy)ethyl phosphate, which is commercially available from Aldrich Chemical Company, St. Louis Mo., or Polymer Science Inc. Another preferred ester is the bis(2-(methacryloxy)ethyl) phosphate, having the above structure wherein n is 2.

Other ethylenically unsaturated phosphoric acid esters or phosphoric acid ester derivates may optionally be added to the dental restorative composition, including, for example, vinyl phosphonic acids, vinyl phosphinic, vinyl phosphenic acids, phosphoric acids, alkoxylated phosphoric acids, polyphosphoric acids, and alkoxylated polyphosphoric acids, fluorinated phosphoric acids, phosphoric acid esters of oils, phosphinic acids, alkylphosphinic acids, aminophosphinic acids, polyphosphinic acids, vinyl phosphinic acids, phosphonic acids, polyphosphonic acids, phosphonic acid alkyl esters, α-phosphono fatty acids, organoamine polymethylphosphonic acids, organoamino dialkylene phosphonic acids, alkanolamine phosphonic acids, trialkyldiene phosphonic acids, acylamidomethane phosphonic acids, alkyliminodimethylene diphosphonic acids, polymethylene-bis (nitrilo dimethylene)tetraphosphonic acids, alkyl bis (phosphonoalkylidene) amine oxide acids, esters of substituted aminomethylphosphonic acids, phosphonamidic acids, and mixtures comprising at least one of the foregoing.

The ethylenically unsaturated phosphoric acid ester is present in an amount of about 1 to about 50 wt %, based on the total weight of the total curable organic component. Within this range, a concentration of less than or equal to about 40 wt % can be employed, with less than or equal to about 30 wt %, based on the total weight of the total curable resin component, being more preferred. Also preferred within this range is a concentration of greater than or equal to about 3, with greater than or equal to about 5 wt %, based on the total weight of the total curable resin component, being especially preferred.

Water is also present in the dental composition in an amount of about 1 to about 50 wt %, based on the total weight of the dental composition. Within this range, a concentration of less than or equal to about 30 can be employed, with less than or equal to about 2 wt %, based on the total weight of the dental composition, being more preferred. Also preferred within this range is a concentration of greater than or equal to about 5, with greater than or equal to about 10 wt %, based on the total weight of the dental composition, being especially preferred. Water serves as is a diluent for the liquid two-part compositions. Water may also facilitate the reaction between the ethylenically unsaturated phosphoric acid ester and the surface reactive glass.

The filler component contains a surface reactive glass, and optionally, other known polymeric or inorganic fillers. Suitable surface reactive glasses for use in the filler component can be obtained from Industrial Corporation or from Schott Glass Electronic Packaging Company, and typically comprise aluminosilicate glass powders containing at least one element selected from Ca, Sr, and Ba. Preferred examples include fluoroaluminosilicate glass powders having an average particle size of about 0.2 to about 10 micrometers, which are capable of releasing fluorine, and comprise, based on the total weight of the glass, about 20 to about 50% by weight of $SiO_2$, about 20 to about 40% by weight of $Al_2O_3$, about 15 to about 40% by weight of BaO, and about 1 to about 20% by weight of $F_2$ as described in Published Japanese Patent Application No. 55882/1995. Furthermore, the surface reactive glass may also include a lanthanide metal element such as, for example, La, Gd, and/or Yb, if desired. Preferably, the surface reactive glass component forms a reaction product with the phosphoric acid ester, and exhibits an ability to release fluorine when part of a dental restoration.

In addition to the surface reactive glass, the filler composition may also comprise one or more other organic or inorganic fillers, including those currently used in dental restorations and restoratives. Preferred additional fillers include those capable of being covalently bonded to the curable resin component itself or to a coupling agent that is covalently bonded to both. Examples of suitable fillers include, but are not limited to, silica, quartz, strontium silicate, strontium borosilicate, lithium silicate, lithium alumina silicate, amorphous silica, ammoniated or deammoniated calcium phosphate, alumina, zirconia, tin oxide, and titania. Particularly suitable fillers are those having a particle size of about 0.1 to about 5.0 micrometers, and are mixed with a silicate colloid of about 0.001 to about 0.07 micrometers. Some of the aforementioned inorganic fillers and methods of preparation thereof are disclosed in U.S. Pat. Nos. 4,544,359 and 4,547,531, pertinent portions of which are incorporated herein by reference. Calcium phosphates is preferred for use herein, calcium phosphate and tricalcium phosphate being more preferred.

The filler component may also include radiopaque/high refractive index materials, for example, apatites. Suitable high refractive index fillers include, but are not limited to, high refractive index silica glass fillers; calcium silicate based fillers such as apatites, hydroxyapatites or modified hydroxyapatite compositions. Alternatively, inert, non-toxic radiopaque materials, such as bismuth oxide ($Bi_2O_3$), barium sulfate, and bismuth subcarbonate may be used. Suitable fillers have a particle size of about 0.1 to about 5.0 micrometers, and may further comprise unbound silicate colloids having an average particle size of about 0.001 to about 0.07 micrometers. These additional fillers may also be silanized. Some of the aforementioned inorganic fillers and methods of preparation thereof are disclosed in U.S. Pat. Nos. 4,544,359 and 4,547,531, pertinent portions of which are incorporated herein by reference.

The surface reactive glass component comprises 10 to 100 wt % of the total filler component. Within this range, a concentration of less than or equal to about 80 wt % can be employed, and less than or equal to about 60 wt % is more preferred. Also preferred within this range is a concentration of greater than or equal to about 10, with greater than or equal to about 30 wt %, based on the total weight of the filler component, is being especially preferred.

The amount of total filler component in the dental composition can vary widely depending on the intended use, being about 1 to about 90 wt %, based on the total weight of the composition. The amount of filler component used may be determined by the requirements of the particular application. Thus, for example, cavity filling materials generally comprise about 60 to about 90 wt % filler; luting cements comprise about 20 to about 80 wt % filler; sealants generally comprise about 1 to about 20 wt % filler; adhesives generally comprise about 1 to about 30 wt % filler; and restoratives comprise about 50 to about 90 wt % filler, with the remainder in all cases being the other components of the dental composition.

In addition to the above monomers and oligomers, the dental resin composition also includes a curing system, comprising polymerization initiators, polymerization accelerators, and/or the like. Suitable polymerization initiators include initiators known in the art. For example, visible light curable compositions employ light-sensitive compounds including but not being limited to benzil, benzoin, benzoin methyl ether, DL-camphorquinone (CQ), benzil diketones and acylphosphine oxides. Either UV-activated cure or visible light-activated cure (approximately 230 to 750 nm) is acceptable. The amount of photoinitiator is selected according to the curing rate desired. A minimally catalytically effective amount is generally about 0.01 wt %, based on the total weight of the curable organic component, and will lead to a slower cure. Faster rates of cure may be achieved with amounts of catalyst of greater than or equal to about 0.01 wt % to about 5 wt %, based on the total weight of the curable organic component.

Alternatively, the composition may be formulated to be self-curing. Self-curing compositions will generally contain free radical polymerization initiators such as, for example, a peroxide in an amount of about 0.05 to about 4.0 wt % of the total weight of the curable resin component. Preferred free radical initiators include lauryl peroxide, tributyl hydroperoxide, and the like, with a benzoyl peroxide being more preferred. Other reducing agents suitable for self-cure polymerization initiations are salts of sulfinic acid, for example, the sodium salt of benzenesulfinic acid.

Polymerization accelerators suitable for use include various organic tertiary amines well known in the art. In visible light curable compositions, for example, tertiary amines are generally acrylate derivatives, such as dimethylaminoethyl methacrylate and, particularly, diethylaminoethyl methacrylate (DEAEMA) in an amount of about 0.05 to about 0.5 wt %. In the self-curing compositions, the tertiary amines are generally aromatic tertiary amines, preferably tertiary aromatic amines such as ethyl 4-(dimethylamino)benzoate (EDMAB), 2-[4-(dimethylamino)phenyl] ethanol, N,N-dimethyl-p-toluidine (DMPT), bis(hydroxyethyl)-p-toluidine, and triethanolamine. Such accelerators are generally present at about 0.1 to about 4.0 wt % based on the total weight of the curable resin component.

Other additives may also be present in the dental resin composition, including, for example, ultraviolet light absorbers, antioxidants, and other additives well known in the art. It is preferred to employ an ultraviolet absorber at about 0.05 to about 5.0 wt %, based on the total weight of the dental composition. Such UV absorbers are particularly desirable in the visible light curable compositions in order to avoid discoloration of the resin from any incident ultraviolet light. Suitable UV absorbers include, for example, various benzophenones, particularly UV-5411 available from American Cyanamid Company.

The above described dental composition may be provided to the practionioner in the form a single composition, wherein the curing reaction may be triggered shortly before usage in dental restorative applications by the utilization of, for example, visible light, UV light and/or increased temperature. When formulated as a one-part composition, preferably, the single admixture does not separate during normal storage.

Alternatively, the components may be provided to the practioner as a multiple-component composition wherein two or more component combinations are mixed just prior to use. Examples of multiple component compositions include, for example, one component combination including an acrylate or methacrylate resin, methacrylate terminated phosphoric acid ester, and water, and the other component combination including a diluent acrylate or methacrylate monomer, a reactive glass, an initiator, an accelerators, and the like. A preferred two-part formulation provides the liquid components (e.g., curable organic component and water) as one part, and the dry components (e.g., fillers and initiators) as a second part. In an especially preferred embodiment, a the compostion is formulated to provide UV and/or visible light curing together with self-curing. Such compositions are most conveiniently provided to the practitioner in two parts.

In use, the compositions are provided to the practitioner who applies them to the appliance or to the site to be restored by methods known in the art. After application, the compositions are cured, either through a self-cure process, exposure to UV and/or visible light, or a combination thereof.

Dental restorations made using the above-described compoistions display good aesthetics, improved mechanical properties such as strength and wear resistance, long-term fluoride release, and a small amount of hygroscopic expansion. As a result, longer-lasting restorations can be obtained with applications being extended to areas of the oral cavity subjected to moderate to high stresses. The various embodiments of this disclosure are further illustrated by the following non-limiting examples.

EXAMPLES

Several examples of a dental restorative composition in accordance with the present disclosure were prepared comprising the components shown in Tables 1 and 2 below, wherein amounts are given in parts per hundred based on the total weight of each composition set forth in the Table.

TABLE 1

Resin-Modified Glass Ionomer Liquid Dental Restorative Compositions

| Compositions | L1 | L2 | L3 | L4 | L5 |
|---|---|---|---|---|---|
| bis-HEMA phosphate[1] | 3.33 | 22.2 | 15.6 | 6.24 | 3.12 |
| acrylic acid co-polymer[2] | — | — | — | 20 | 20 |
| bis-GMA | | 26.7 | 29.8 | 5.96 | 2.98 |
| PUDMA | 17.5 | | | | 8.0 |
| PEGDMA | 32.5 | 40 | 44.6 | 40 | 40 |
| EBPDMA (30)[3] | — | — | — | 23.8 | 23.9 |
| Water | 16.7 | 11.1 | 10 | 4 | 2 |
| Lucirin-TPO | 0.5 | 0.5 | 0.74 | 0.45 | 0.42 |
| CQ | 0.12 | 0.12 | 0.12 | 0.13 | 0.08 |
| BHT[4] | 0.01 | 0.01 | 0.005 | 0.01 | 0.01 |

[1]Bis(2-(methacryloxy)ethyl) phosphate, available from Aldrich Chemical Company, St. Louis Mo.
[2]50% Solution available from Esstech Co. under the product code of 167 000.
[3]A hydrophilic and highly ethoxylated bisphenol dimethacrylate resin (d = 30), available from Sartomer Exton, Pennsylvania under the product code of SR9036.
[4]Butylated hydroxytoluene, Aldrich Chemical Company, St. Louis Mo.

TABLE 2

Powder Composition

| Compositions | P1 | P2 | P3 | P4 |
|---|---|---|---|---|
| Silane treated barium glass | — | 50 | 40 | 39.5 |
| Ca—F—Al-silicate | 100 | 50 | 60 | 59.5 |
| Fumed silica | | | | 1 |
| Sodium salt, sulfinic acid | 1.5 | 1.5 | 1.5 | 0.67 |
| Benzoyl peroxide | 1.5 | 1.5 | 1.5 | 0.67 |
| DHEPT[1] | — | — | — | 0.15 |

[1]Dihydroxyethyl-p-toluidine

To prepare the specific examples shown in Table 3, 2 drops of liquid from Table 1 were mixed with one scoop of the powder listed in Table 2, using the scoop and liquid vial available from Pentron Corp., Wallingford, Conn. Each sample was capable of three-way curing. The comparative example cements listed in Table 3 were powder-liquid chemical cured, and prepared according to the manufacture's instructions.

Compressive strength testing was conducted using cylinders of 5 mm in diameter and 10 mm in height. Five samples each were tested. The tests were conducted using a crosshead speed of 0.2 inches per minute after the material was allowed to "set" for one hour.

The water solubility test samples were discs of about 15 mm diameter and about 1 mm thickness. The tests were performed according to ISO Standard 7489 "Dental Glass Polyalkenoate Cements".

TABLE 3

Properties of the Resin-Modified Glass Ionomer Dental Restorative Compositions

| Example | Curing mode | Compressive Strength at one hour MPa (SD) | Water Solubility 7 days (wt. %) |
|---|---|---|---|
| L1/P1 | self-cure only | 50.2 (3.5) | — |
| L1/P1 | light curing first | 72.5 (4.1) | — |
| L1/P2 | self-cure only | 62.3 (4.2) | — |
| L1/P2 | light curing first | 81.3 (5.4) | — |
| L2/P1 | self-cure only | 55.4 (4.5) | — |
| L2/P1 | light curing first | 88.1 (3.2) | — |
| L2/P2 | self-cure only | 85.6 (5.0) | — |
| L2/P2 | light curing first | 113 (8.1) | — |
| L3/P3 | self cure only | 63.7 (4.9) | 5.1 (0.3) |
| L4/P4 | self cure only | 65.2 (5.3) | |
| L5/P4 | self cure only | 75 (7.4) | 4.5 (0.6) |
| Rel X Luting Cement [1] | self cure only | 54.5 (7.1) | 7.9 (0.5) |
| VivaGlass Cement [2] | self cure only | 58.5 (11.4) | |
| Zinc Polycarboxylate Cement [3] | self cure only | 31.6 (4.1) | 11.6 (0.3) |
| Zinc Phosphate Base Cement [4] | self cure only | 36.7 (3.8) | 12.5 (0.6) |

[1] Comparative Example-available from 3M, St. Paul, Minnesota
[2] Comparative Example-available from Vivadent/Ivoclar Schaan, Liechtenstein
[3] Comparative Example-available under the trade name Durelon ™ from 3M (ESPE), St. Paul, Minnesota
[4] Comparative Example-available from Fleck's Zinc Cement (Mizzy, Inc., NJ)

As the above data show, the dental compositions as described herein provide compressive strength at or above that of comparative examples.

While preferred embodiments have been shown and described, various modifications and substitutions may be made thereto without departing form the spirit and scope of the invention. Accordingly, it is to be understood that the present invention has been described by way of illustration and not limitation.

What is claimed is:

1. A curable dental restorative composition comprising
about 1 to about 90 wt %, based on the total weight of the composition, of a filler component, the filler component comprising
about 10 to 100 wt %, based on the total weight of the filler component, of a surface reactive glass, and up to about 90 wt %, based on the total weight of the filler component, of other organic or inorganic filler;
about 1 to about 50 wt %, based on the total weight of the composition, of water; and
about 10 to about 98 wt %, based on the total weight of the composition, of a curable organic component, the curable organic component comprising
about 50 to about 99 wt %, based on the total weight of the curable organic component, of an ethylenically unsaturated resin component,
about 1 to about 50 wt %, based on the total weight of the curable organic component, of an ethylenically unsaturated phosphoric acid ester; and
about 0.02 to about 5 wt %, based on the total weight of the curable organic component, of a curing system.

2. The dental restorative composition of claim 1, wherein the ethylenically unsaturated resin component comprises a polyurethane dimethacrylate, a diurethane dimethacrylate, a polycarbonate dimethacrylate, an ethoxylated bisphenol A dimethacrylate, Bis-GMA, a diluent monomer, a carboxylated polymer, or a combination comprising at least one of the foregoing.

3. The dental restorative composition of claim 1, wherein the ethylenically unsaturated resin component comprises a hydroxy alkyl methacrylate diluent monomer, an ethylene glycol methacrylate diluent monomer, a diol dimethacrylate monomer, or a combination comprising at least one of the foregoing.

4. The dental restorative composition of claim 3, wherein the diluent is 2-hydroxyethyl methacrylate, 2-hydroxypropyl methacrylate, ethylene glycol methacrylate, diethylene glycol methacrylate, tri(ethylene glycol) dimethacrylate, tetra(ethylene glycol) dimethacrylate, butanedioldimethacrylate, dodecanedioldimethacrylate, 1,6-hexanedioldiniethacrylate, or a combination comprising at least one of the foregoing.

5. The dental restorative composition of claim 1, wherein the ethylenically unsaturated phosphoric acid ester component comprises an unsaturated acrylate terminated phosphoric acid ester, a methacrylate terminated phosphoric acid ester, or a combination comprising at least one of the foregoing.

6. The dental restorative composition of claim 1, wherein the ethylenically unsaturated phosphoric acid ester component is represented by the formula:

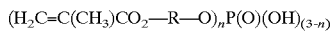

$$(H_2C{=}C(CH_3)CO_2{-}R{-}O)_nP(O)(OH)_{(3-n)}$$

wherein n=1 or 2 and K is a divalent alkyl or aryl group having en one to about 36 carbon atoms.

7. The dental restorative composition of claim 1, wherein the ethylenically unsaturated phosphoric acid ester comprises 2-(methacryloyloxy)ethyl phosphate.

8. The dental restorative composition of claim 1, wherein the ethylenically unsaturated phosphoric acid ester comprises bis[2-(methacryloyloxy)ethyl]phosphate.

9. The dental restorative composition of claim 8, wherein the ethylenically unsaturated phosphoric acid ester component further comprises a vinyl phosphonic acid, a vinyl phosphinic acid, a vinyl phosphenic acid, a phosphoric acid, an alkoxylated phosphoric acid, a polyphosphoric acid, an alkoxylated polyphosphoric acid, a fluorinated phosphoric acid, a phosphoric acid ester of oil, a phosphinic acid, an alkylphosphinic acid, an aminophosphinic acid, a polyphosphinic acid, a vinyl phosphinic acid, a phosphonic acid, a polyphosphonic acid, a phosphonic acid alkyl ester, an α-phosphono fatty acid, an organoamine polymethylphosphonic acid, an organoamino dialkylene phosphonic acid, an alkanolamine phosphonic acid, a trialkyldiene phosphonic acid, an acylamidomethane phosphonic acid, an alkyliminodimethylene diphosphonic acid, a polymethylene-bis(nitrilo dimethylene)tetraphosphonic acid, an alkyl bis(phosphonoalkylidene) amine oxide acid, an ester of substituted aminomethylphosphonic acid, a phosphonamidic acid, or a combination comprising at least one of the foregoing.

10. The dental restorative composition of claim 1, wherein the surface reactive glass component is a fluoroaluminosilicate glass, comprising;

about 20 to about 50% by weight $SiO_2$;

about 20 to about 40% by weight of $Al_2O_3$;

about 15 to about 40% by weight of BaO;

about 1 to about 20% by weight $F_2$; and has a particle size having a major axis of about 0.2 to about 10 micrometers.

11. The dental restorative composition of claim 1, wherein the surface reactive glass component comprises an aluminosilicate glass powder comprising Ca, Sr, Ba, or a combination comprising at least one of the foregoing.

12. The dental restorative composition of claim 1, wherein the other filler comprises silica, quartz, strontium silicate, strontium borosilicate, lithium silicate, lithium alumina silicate, amorphous silica, ammoniated calcium phosphate, deammoniated calcium phosphate, alumina, zirconia, tin oxide, titania, apatite, high refractive index silica glass, calcium silicate, hydroxyapatite, modified hydroxyapatite, bismuth oxide, barium sulfate, bismuth subcarbonate, or a combination comprising at least one of the foregoing.

13. The dental restorative composition of claim 1, wherein the other inorganic tiller comprises silica having a particle size having a major axis of about 0.1 to about 5.0 micrometers, and a silicate colloid having particles with a major axis of about 0.001 to about 0.07 micrometers.

14. The dental restorative composition of claim 1, wherein the curing system comprises a UV or visible light polymerization initiator, a polymerization accelerator, and a self-cure polymerization initiator.

15. The dental restorative composition of claim 1, wherein the composition comprises a single admixture of components.

16. The dental restorative composition of claim 1, wherein the composition comprises two or more separate admixtures of components, and wherein the curing reaction is initiated by mixing the two or more admixtures of components together, by the visible light, by ultraviolet light, by an increased temperature, or a combination comprising at least one of the foregoing.

17. A method of forming a dental restoration comprising:

applying the dental restorative composition of claim 1 to a site to be restored; and curing the dental restorative composition.

18. A method of forming a dental restoration, comprising:

combining the separate admixtures of components of the dental restorative composition of claim 16 to form a dental restorative composition, applying the dental restorative composition to a dental appliance; and curing the dental restorative composition.

19. A dental restoration fanned from the curable dental restorative composition of claim 1.

20. The dental restoration of claim 19, wherein the reactive glass component releases fluorine from the dental restoration.

* * * * *